United States Patent
Kyriakou (10) Patent No.: US 9,554,766 B2
(45) Date of Patent: Jan. 31, 2017

(54) REDUCING ARTIFACTS IN AN IMAGE DATA SET AND X-RAY DEVICE

(71) Applicant: Yiannis Kyriakou, Spardorf (DE)

(72) Inventor: Yiannis Kyriakou, Spardorf (DE)

(73) Assignee: Siemens Aktiengesellschaft, München (DE)

( * ) Notice: Subject to any disclaimer, the term of this patent is extended or adjusted under 35 U.S.C. 154(b) by 156 days.

(21) Appl. No.: 14/476,331

(22) Filed: Sep. 3, 2014

(65) Prior Publication Data

US 2015/0078507 A1 Mar. 19, 2015

(30) Foreign Application Priority Data

Sep. 19, 2013 (DE) .......................... 10-2013-218819

(51) Int. Cl.
*G06K 9/00* (2006.01)
*A61B 6/00* (2006.01)
(Continued)

(52) U.S. Cl.
CPC .............. *A61B 6/5258* (2013.01); *A61B 6/032* (2013.01); *A61B 6/4085* (2013.01); *A61B 6/505* (2013.01); *G06T 5/002* (2013.01); *G06T 5/50* (2013.01); *G06T 7/0083* (2013.01); *G06T 7/0097* (2013.01); *G06T 11/008* (2013.01);
(Continued)

(58) Field of Classification Search
CPC ..... A61B 6/032; A61B 6/4085; A61B 6/4441; A61B 6/505; A61B 6/5258; G06T 11/008; G06T 2207/10081; G06T 2207/20061; G06T 2207/20224; G06T 2207/30008; G06T 5/002; G06T 5/50; G06T 7/0083; G06T 7/0097
See application file for complete search history.

(56) References Cited

U.S. PATENT DOCUMENTS

| 2005/0010106 A1* | 1/2005 | Lang ..................... A61B 6/469 600/425 |
| 2011/0007956 A1 | 1/2011 | Meyer et al. |
| 2013/0343623 A1* | 12/2013 | Fan ..................... G06T 11/005 382/131 |

FOREIGN PATENT DOCUMENTS

DE 102009032059 A1 1/2011

OTHER PUBLICATIONS

Prell, D., et al. "Metal artifact reduction for clipping and coiling in interventional C-arm CT." American Journal of Neuroradiology 31.4 (2010): 634-639.*

(Continued)

Primary Examiner — Nirav G Patel
(74) Attorney, Agent, or Firm — Lempia Summerfield Katz LLC (57) ABSTRACT

Streak artifacts generated by at least one X-ray attenuating object arranged outside a reconstruction volume in a three-dimensional image data set showing the reconstruction volume are reduced. The reconstruction volume is reconstructed from two-dimensional projection images recorded from different projection directions. The object is localized in the projection images showing the object. To determine corrected projection images for the reconstruction of the image data set, the image data of the area of each projection image showing the object is corrected to remove the object. The localization of the object is performed taking into account difference images of the measured projection images and from a reconstruction data set of forward-projected comparative images reconstructed from the measured projection images.

20 Claims, 3 Drawing Sheets (51) Int. Cl.
   *A61B 6/03*      (2006.01)
   *G06T 5/00*      (2006.01)
   *G06T 5/50*      (2006.01)
   *G06T 7/00*      (2006.01)
   *G06T 11/00*     (2006.01)

(52) U.S. Cl.
   CPC ... *A61B 6/4441* (2013.01); *G06T 2207/10081* (2013.01); *G06T 2207/20061* (2013.01); *G06T 2207/20224* (2013.01); *G06T 2207/30008* (2013.01)

(56) References Cited

OTHER PUBLICATIONS

Prell, Daniel, et al. "A novel forward projection-based metal artifact reduction method for flat-detector computed tomography." Physics in medicine and biology 54.21 (2009): 6575.*
German Office Action dated Mar. 28, 2014 for corresponding DE 10 2013 218 819.6 with English Translation.
E. Meyer et al., "Normalized Metal Artifact Reduction (NMAR) in Computed Tomography," In: Nuclear Science Symposium Conference Record (NSS/MIC), pp. 1-5, 2009.

* cited by examiner

REDUCING ARTIFACTS IN AN IMAGE DATA SET AND X-RAY DEVICE

RELATED CASE

This application claims the benefit of DE 102013218819.6, filed on Sep. 19, 2013, which is hereby incorporated by reference in its entirety.

TECHNICAL FIELD

The present embodiments relate to reducing artifacts generated by at least one X-ray attenuating object arranged outside a reconstruction volume in a three-dimensional image data set.

BACKGROUND

Artifacts in image data sets recorded with X-rays that are reconstructed from projection images may originate in objects of higher density lying inside or outside the reconstruction volume. Objects of this kind generally have a higher density and/or a higher attenuation coefficient than naturally occurring materials in the body of a person, which is usually recorded as the object under examination. Such artifacts are particularly frequently artifacts resulting from metal objects and so may also be designated metal artifacts.

To date, a plurality of methods have been suggested for correcting or avoiding metal artifacts or other artifacts resulting from strongly attenuating objects when the object is located within the actual reconstruction volume. In this case, it is usual to segment the object in the image data set or a previously reconstructed reconstruction data set of the reconstruction volume. In this way, the voxels included in the object are identified in the three-dimensional reconstruction volume and also located in the two-dimensional projection images by forward projection. An interpolation method may be used to compensate the object traces, in particular metal traces, in the projection images. The final image data set is then generated during a second reconstruction using the corrected projection images. In this way, the second reconstruction contains fewer metal artifacts than the first reconstruction. Here, it is generally the case that the quality of the correction method is mainly determined by the quality of the segmentation of the object in the reconstruction data set of the first reconstruction.

However, this concept cannot be used if the object giving rise to the artifacts does not appear in the reconstruction volume (nominal measuring field). Here, the reconstruction volume is the area covered by all the projection images (e.g., usually by a projection image interval of at least 180°, in particular 180° plus the fan angle). The reconstruction volume is the area that is ultimately also to be reconstructed in the image data set while the projection data is not complete for all objects and structures outside the reconstruction volume so that it is also not possible to produce a complete and correct depiction of the objects. However, it is also the case that when objects, in particular metal objects, are present outside the reconstruction volume, for example fixation screws, markers and the like, the objects are also able to generate artifacts in a reconstructed image data set for the reconstruction volume since these objects may be seen in at least a part of the projection images that are a part of the raw data. Even if only a few projection images represent the object, it is still possible for the object to give rise to artifacts.

To date, there has been no practicable solution for effective artifact correction where an object is located outside the reconstruction volume. The known methods work on the basis of a segmentation of the objects in the three-dimensional reconstruction volume. Methods are also known which use a raw-data-based estimation of the positions of objects in sinograms. These methods also do not produce satisfactory results when the objects are only visible in a few projection images.

SUMMARY AND DESCRIPTION

The scope of the present invention is defined solely by the appended claims and is not affected to any degree by the statements within this summary.

Artifacts generated by artifact-generating objects located outside the reconstruction volume in three-dimensional image data sets reconstructed from projection images are reduced, enabling the image quality to be increased.

The object in the projection images showing the object is localized, and, to determine corrected projection images for the reconstruction of the image data set, the image data of the area of each projection image showing the object is corrected to remove the object. The localization of the object is performed taking into account difference images of the measured projection images and from a reconstruction data set of forward-projected comparative images reconstructed from the measured projection images.

Instead of the localization of objects in actual measured projection images, difference images are derived from the projection images by deducting forward-projected comparative images and are considered. Here, two evaluation possibilities for the difference images exist. On the one hand, the improved localizability of strongly attenuating objects in difference images is utilized and, on the other, the difference images may be used within the context of an iterative reconstruction of a volume, which also contains the object. Common to the two alternatives is the fact that the use of the difference images ultimately results in the localization of objects, in particular metal objects, outside the reconstruction volume, that is the nominal measuring field. It is, therefore, also possible to identify the pixels relating to the object in the projection images and correct them correspondingly, wherein procedures that are in principle known, in particular for interpolation, may be used in order ultimately to obtain corrected projection images. These may then be used for the reconstruction of an improved three-dimensional image data set. Therefore, the artifact reduction procedures may be combined at will with other metal-artifact-correction mechanisms.

Here, the reconstruction volume may be defined as being contained in all the projection images, therefore as being completely covered. Other definitions may also provide that it is sufficient for the reconstruction volume to be covered in an angular interval, in particular 180°, plus the fan angle of the radiation source, and so Tuy's condition for complete reconstruction is fulfilled. Therefore, the reconstruction volume may also be generally described as the nominal measuring field.

It is also generally established that the object has a higher density and/or a higher attenuation coefficient than all naturally occurring materials in the body of a person, such as the object being a metal object. Objects of this kind may particularly frequently give rise to artifacts, in particular so-called streak artifacts, which may be corrected even if the object is located outside the reconstruction volume.

As already mentioned, the present embodiments have two different manifestations, or alternative embodiments. The first of these embodiments is based on the knowledge that an approach that attempts to localize the artifact-causing objects in the actual projection images is less robust and less suitable as the basis for an artifact-reducing method. This reason for this is that the courses of the image data in the two-dimensional projection images are determined by complex combinations in the reconstruction volume, and possibly also outside this, and therefore may also have edges, jumps in intensity and the like without the occurrence of objects. In this context, the first embodiment suggests that it be attempted to localize objects in difference images, which are generated by forward-projected comparative images that do not actually contain the object. Therefore, it is provided in the first embodiment that the reconstruction data set be determined by reconstruction of the reconstruction volume from the measured projection images. It may then be provided that the object-showing areas in the difference images are segmented while the other structures depicted have already been extensively removed.

In particular, it may, therefore, also be said that the first embodiment relates to a method of the type mentioned in the introduction in which the object is localized in the projection images showing the object and, to determine corrected projection images for the reconstruction of the image data set, the image data of the area of each projection image showing the object is corrected to remove the object. For the localization of the object in difference images of the measured projection images and from a reconstruction image data set of forward-projected comparative images reconstructed by reconstruction of the reconstruction volume from the measured projection images, the areas showing the object are segmented.

Therefore, in the first embodiment, there is initially a reconstruction of the recorded raw data to the reconstruction volume. As result of the reconstruction, a reconstruction data set is obtained. Although the reconstructed data set includes the artifacts arising from the object, the reconstructed data set does not show the actual object. Then, a forward projection of the reconstruction data set is performed for the measuring geometry that is in the directions in which projection images were recorded. The projection images that were measured contain the object, which, when the object gives rise to artifacts, is an object with high density and/or high attenuation coefficients. If the measured projection images and the forward-projected comparative images are now subtracted, a large difference occurs at the points where the object, in particular metal, is present. In the (in reality, non-existent) ideal case, the only difference between the comparative images and the measured projection images is the object. In practice, this is not the case so that the difference images formed are analyzed again in order to segment the areas showing the object (object traces).

In a specific embodiment, an edge detection algorithm is used for the segmentation. In this case, it is assumed that it is relatively easy to identify the borders of the object in the difference profiles since portions contained in the reconstruction volume have already been subtracted out. For example, in this case, it may be provided that a gradient of the difference images is examined for local minima and/or maxima. Suitable threshold values for the detection of objects are established. In this context, it may be expedient to perform a correlation analysis to identify interconnected areas belonging to the object.

A further improvement of the segmentation may be achieved if a segmentation of the reconstruction data set is performed according to at least two material classes with assigned attenuation coefficients. A virtual normalization image based on effective transmission lengths of the material classes is determined in the projection directions of the projection images for which a comparative image is determined. Prior to the formation of the difference images, the measured projection images and the comparative images are normalized using the normalization images, wherein the corrected measured projection images are denormalized after the removal of the object. Since further objects and/or structures, which generate a strong signal and simultaneously may also influence the errors sought, that is the difference images, may be present in the projection images, this development of the method provides for a normalization to take place. In this case, the measured projection images may be normalized with a reconstruction data set segmented according to a plurality of material classes prior to the subtraction. In this case, it can, for example, be provided that the segmentation of the reconstruction data set is performed according to four material classes, in particular air, soft tissue, bone and contrast medium. If no contrast medium is used, three-material segmentation may also suffice. The normalization and later denormalization cause areas, for example those containing bone and the like, which are present in the measured projection images and the comparative images, but still have small differences, to be attenuated. The only components that are not attenuated with this procedure are the objects, which are not contained in the comparative images. In this way, the calculation of the difference and the subsequent determination of the object traces, that is the segmentation, are further simplified. With respect to the techniques for normalization and denormalization, reference is made by way of example to an article by Esther Meyer et al. "Normalized metal artifact reduction (NMAR) in computed tomography", Med. Phys. 37, 5482 (2010).

Here, there is a general reference to the fact that for an interpolation-based artifact correction on the measured projection images, the intensity of the depiction of the object, that is the image data, is not relevant. Instead, it is only necessary to determine the metal traces for a specific measured projection image that is a specific recording geometry. Therefore, it is also not relevant whether object intensities are forward-projected correctly. As long as the method provides clear segmentation in the measured projection images, it is possible to continue with the removal of the object as known from the prior art. In this case, it is also possible in both embodiments to use interpolation with any methods desired, wherein it is also possible to use the afore-mentioned four-material segmentation or three-material segmentation in order to determine new images (projection data) in the areas of the projection images depicting the object. The areas correspond as precisely as possible to the projection data which would be measured if the object did not exist.

According to the second of the alternative embodiments, it is provided that the reconstruction data set for an object volume containing the object that is larger than the reconstruction volume. In an iterative method in each case, a three-dimensional correction data set is reconstructed from the difference images based on the current reconstruction data set and added to the current reconstruction data set to form a new reconstruction data set. Following the occurrence of an abort criterion, the object in the most recently determined reconstruction data set is segmented and the segmentation in the reconstruction data set is used for the localization of the object in the measured projection images.

In the second embodiment, the determination of the difference is therefore defined as a type of iterative process. In this case, the comparative images are calculated from a reconstruction data set including an artificially larger volume than the reconstruction volume, namely the object volume. In this case, therefore, voxels are also acquired in which there is no sufficient cover by measured projection images. In this case, the object volume is defined such that the at least one object is acquired, even if the object is "smeared" since the recorded projection data is not sufficient for an exact reconstruction. However, the result of this is that the forward-projected comparative images from the reconstruction data set also do not contain the object in an incorrect form so that differences from the measured projection images occur. The concept is now, in order to localize the object as precisely as possible, to locate a reconstruction data set that depicts the object so well that the image data in the difference images is minimized. Therefore, it may be provided that the abort condition used is a minimization of a statistical variable of the image data contained in the difference images, wherein the statistical variable may be an L1 standard or an L2 standard of the image data of the difference images. In this case, the use of the L2 standard is preferred since this achieves a smoother image. In this case, it is noted that, it is additionally or alternatively also possible to use other abort conditions, for example exceeding a prespecified number of iterations and the like.

Overall, therefore, the second embodiment describes an iterative, constantly self-improving reconstruction that is aimed at depicting the object as accurately as possibly at least with respect to the position despite the incomplete depiction in the measured projection images. The object may then be segmented in the reconstruction data set and the forward projection of the object in this optimized reconstruction data set provides the metal traces in the measured projection images, that is the desired segmentation, in order to remove the object in the measured projection images.

With an iterative reconstruction process of this kind, it may be provided that a virtual X-ray detector is defined corresponding to the measuring field that would be necessary in order sufficiently to cover and completely reconstruct the object volume. In this geometry, during the iterations, the difference between the reconstruction data set and the measured projections is then minimized in that the differences are added up until the optimum is achieved, where the determination of the differences may only be performed for the valid area. An extrapolation of data beyond the valid (i.e. measured by the projection images) area may optionally be performed for the reconstruction. The iterative addition of the differences achieves an improved depiction of the object outside the reconstruction volume.

A preferred development that may be used for both embodiments provides that artifacts generated by the object, in particular streak artifacts, are detected in a reconstruction from the measured projection images based on the reconstruction volume, and a subset of the measured projection images is selected from the geometric properties of the artifacts. Said subset may contain the areas showing the object, and the determination of the difference images and/or the correction to remove the object is restricted to said subset. In this case, therefore, there is a restriction of the measured projection images to be considered, and hence the projection directions to be considered, in that it is estimated from the artifacts still present in the reconstruction data set where the object may be located. This enables minimization of the forward-projection steps and further post-processing. Minimization in particular entails an estimation of the angular position of the object, which means an angular range is indicated in which the object may be seen in measured projection images with a probability exceeding a threshold value. Therefore, the artifacts generated by the object in the reconstruction data set are detected, for example streak artifacts, and their origin is determined in order to obtain an estimation of the position of the object. In the case of streak artifacts, depending upon the recording geometry, the origin may indicate the position of the object, in the simplest case be focused on the object. A Hough transformation may be used to find the artifacts, in particular streak artifacts. If in this way overall the approximate origin of the artifacts, that is the object, is localized and, if it is also assumed that, according to experience, objects of this kind are only present at a few defined positions, the number of measured projection images used for the above method may be significantly minimized so that the calculation time is also minimized.

The method is used for X-ray radiography in cone-beam CT geometry, but may also be used with other constellations.

In addition to the method, embodiments also relate to an X-ray device, in particular a CT-device or a C-arm X-ray device including a control device embodied to perform the method. In this case, the projection images are recorded (measured) with an X-ray radiography arrangement, usually including an X-ray tube and an X-ray detector. To perform the method, the control device may include a reconstruction unit for the determination of the reconstruction data set, and later of the image data set from the corrected projection images, an object-localization unit for the localization of the object taking into account difference images of the measured projection images and forward-projected comparative images from the reconstruction data set and a projection image correction unit, in which, by the removal of the object, the image data of the area of each projection image showing the object is corrected. All the statements with respect to the method may be transferred analogously to the X-ray device with which the aforementioned advantages may also be achieved.

Finally, a computer program, stored as instructions on a non-transitory computer readable medium, executes the method when the program is executed on a computing device, for example the above-mentioned control device. The computer program may be stored on a non-transient storage medium, for example a CD-ROM.

Further advantages and details of the present invention may be derived from the exemplary embodiments described below.

DETAILED DESCRIPTION OF THE PREFERRED EMBODIMENTS

Figures 1, 2:
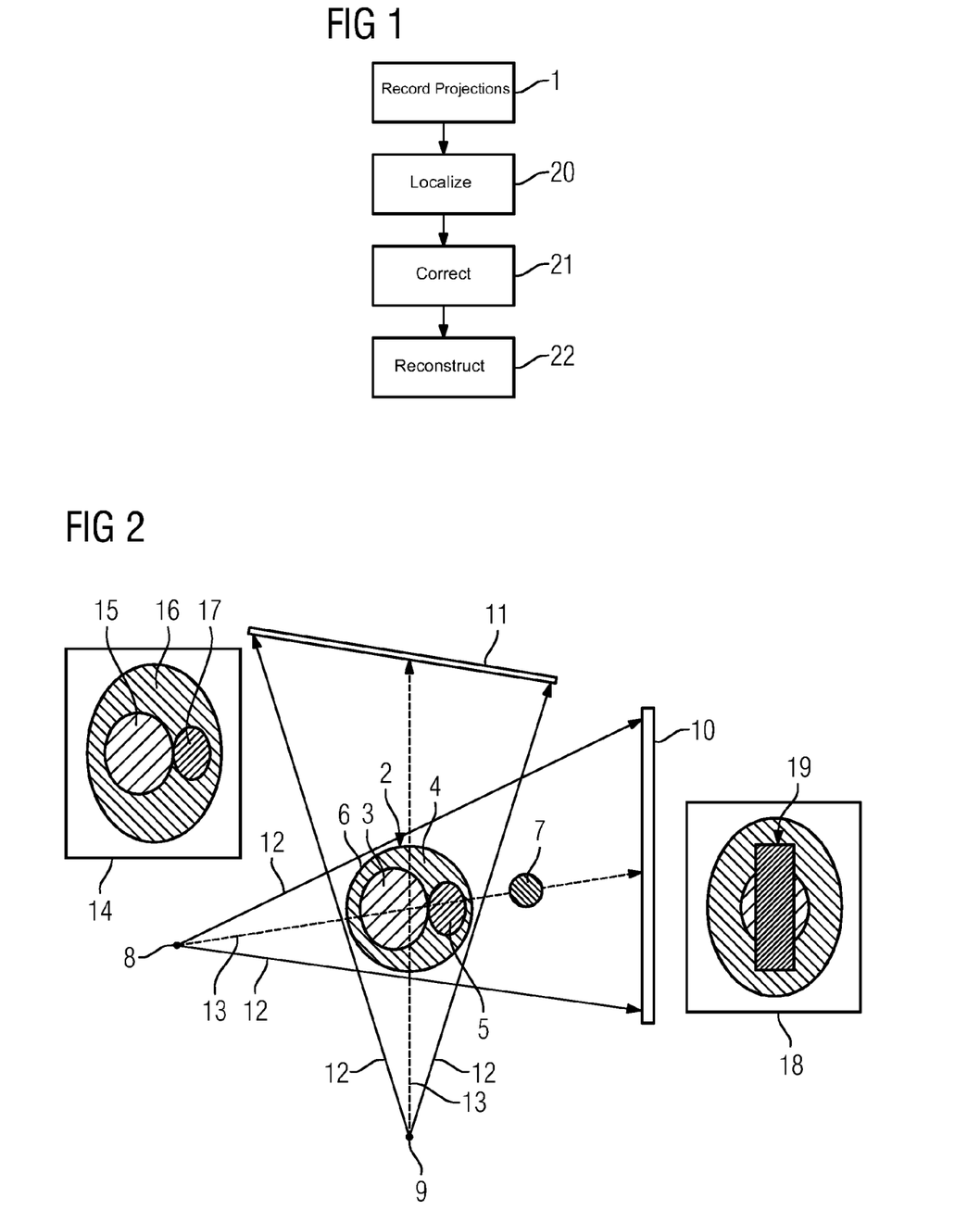
FIG. 1 is a general flow diagram of the method according to one embodiment.
FIG. 2 is a schematic sketch to explain the recording geometry according to one embodiment.

FIG. 1 shows a flow diagram of a general exemplary embodiment of the method. In an act 1, an X-ray recording arrangement of an X-ray device records projection images of an object under examination from different projection directions along a recording trajectory, in particular a circular path segment. In this case, the recording geometry, here a cone-beam geometry, is selected such that a reconstruction volume seen in a final three-dimensional image data set, which is to be reconstructed from the projection images reconstructed, may be seen completely in each measured projection image. For each voxel in the reconstruction volume, Tuy's condition for complete reconstruction is fulfilled. Therefore measured projection images from an angular interval containing 180° and the fan angle are present.

However, in this case, there is also an object outside the reconstruction volume, in this instance a metal object, which may only be seen in a part of the projection images and which may give rise to artifacts during the reconstruction in the reconstruction volume. This recording situation will be explained in more detail by the schematic sketch in FIG. 2.

The center of FIG. 2 shows the object under examination 2 to be recorded, here a part of a patient, that may, for example, contain bone 3, soft tissue 4 and a contrast medium 5, for example iodine. An X-ray recording arrangement is moved around the object under examination 2 so that a completely reconstructable reconstruction volume 6 covered in all the measured projection images results.

Outside this reconstruction volume 6, there is a metal object 7, which, during the reconstruction, may result in the artifacts to be reduced or ideally completely eliminated by the method.

This shows by way of example two positions 8, 9 of the radiation source of the X-ray recording arrangement with the corresponding positions 10, 11 of the X-ray detector.

As may be seen from the perimeter beams 12 in each case, this involves cone-beam geometry. In addition, a dashed line indicates the central beam 13 that ultimately reflects the projection direction.

If the X-ray tube is located at position 9 and the X-ray detector at position 11, a measured projection image 14 is obtained which only shows the object under examination 2. It is possible to identify an area 15, in which the bone 3 is depicted, an area 16 depicting the soft tissue 4, and an area 17 depicting the contrast medium 5.

Another measured projection image 18 is obtained at position 8 for the X-ray tube and position 10 for the X-ray detector. The object 7 lying outside the reconstruction volume 6 is now also recorded so that an area 19 contains image data which shows the object 7.

The concept of the method according to FIG. 1 is now to determine the area 19 as accurately as possible (i.e., to localize the object 7 in the measured projection images 14, 18 so that it is possible to factor the object 7 out of the image data and in this way to obtain corrected projection images).

Therefore, in an act 20 (see FIG. 1), first the object 7 is localized in the measured projection images 14, 18. The areas 9, 10 that show the object 7 in the measured projection images 14, 18 are determined. In both embodiments of the method to be discussed in more detail below, this is performed using difference images, for the creation of which, first a reconstruction data set is determined from the measured projection images 14, 18. From this, comparative images are forward-projected in the measured projection directions so that the difference images may be determined by subtracting the comparative image from the measured projection image 14, 18 for each projection direction. In this case, in a first embodiment of the method, the object traces in the measured projection images 14, 18, that are the areas 19, are determined directly when the reconstruction data set relates to the reconstruction volume 6. In the second embodiment, a larger object volume is reconstructed. The larger object volume includes the reconstruction volume 6 and also the metal object 7. In this case, the depiction of the object 7 in the reconstruction data set is iteratively improved using the difference images until the object 7 may be localized there as precisely as possible and, hence, by forward projection, also in the measured projection images 14, 18.

The subtraction of the images is pixel-based. Each piece of image data of a pixel of the difference image is obtained as the difference between the pixels of the measured projection image 14, 18 and comparative image corresponding to the image data.

If the areas 19 are determined, a correction of the measured projection images 14, 18 may take place in an act 21. To this end, it is possible to use interpolation methods in which, for example, the image data is removed from the areas 19 and replaced by new image data. In a simple case, here linear interpolation is conceivable, however, the image data is preferably determined from other present image data, for example, in that the reconstruction volume 6 in the reconstruction data set is segmented according to different material classes, for example bone, soft tissue, contrast medium and air so that it is also possible to determine effective lengths for the material classes, and hence effective attenuations, for the beams which would strike the object 7, which then only relate to the reconstruction volume 6 and may replace values distorted by the metal object 7.

In an act 22, the three-dimensional image data set is then reconstructed from the corrected projection images.

It is noted that, for both embodiments, the measured projection images 14, 18 to be actually considered may be restricted, which means reduced in number. To this end, a suitable algorithm for streak artifacts, for example a Hough transformation, may be used to detect the artifacts in the reconstruction data set, at least in the portion relating to the reconstruction volume 6. The shape and location of the artifacts may be used to draw conclusions regarding their origin, that is the object 7, and the location of the object 7, so that, for example streak artifacts caused by metal are focused on the metal. In this way, it is possible, to determine a subset of projection images that extremely probably contain areas 19 that show the object 7, wherein the other measured projection images, for example the projection image 14, may be removed from the view. This reduces costs and computing time.

Figure 3:
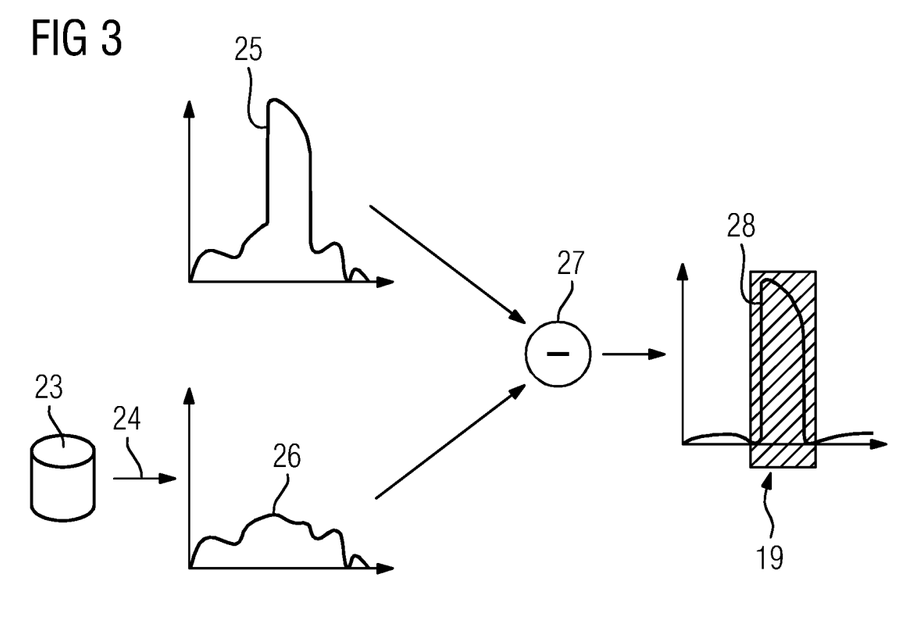
FIG. 3 is a flow diagram for the localization of the object in the first embodiment.

FIG. 3 is a sketch explaining the procedure for the first embodiment in more detail. For purposes of simplicity, here only one-dimensional profiles, for example along a detector line, are shown for the measured projection images 14, 18, the comparative images, and the difference images. In the first embodiment, initially, a reconstruction data set 23 showing the reconstruction volume 6 is determined from the measured projection images 14, 18. From this reconstruction data set 23, it is possible to determine by forward projection comparative images as a type of simulated projection images, arrow 24, wherein a comparative image of this kind is determined for each projection direction examined. The profile 25 now relates to a measured projection image, for example the projection image 18, in which the object 7 is depicted. In the profile 26 of a comparative image, it is possible to identify a difference due to the fact that the object 7 is not contained in the reconstruction data set 23 and hence is also missing in the forward projection. Therefore, it is provided in an act 27 that the comparative images are subtracted from the corresponding measured projection images 14, 18 in order to obtain the difference images, wherein the profile 28 obtained by determining the difference of the profiles 25 and 26 is also shown in FIG. 3. It may be seen that the main portions of the profile 28 lie in the area 19, since, in an ideal case, the area 19 should now only contain the object 7. Therefore, an edge detection algorithm, which may be used to take into account the gradient of the profiles 28 of the difference images and may be examined for minima and maxima, and optionally a correlation analysis, enables the localization of the areas 19 in the difference images (and hence also in the measured projection images 14, 18). All other portions have been removed to a large extent.

The procedure according to FIG. 3 may be further improved in the first embodiment in that the reconstruction data set 23 undergoes segmentation, preferably four-material segmentation according to the material classes air, bone, soft tissue and contrast medium. From the segmentation, a virtual, normalization image based on the effective transmission lengths of the material classes is determined. This normalization image may be used to normalize the measured projection images 14, 18 and the comparative images so that smoothing of the other deviating portions occurs and the method becomes more robust.

Figure 4:
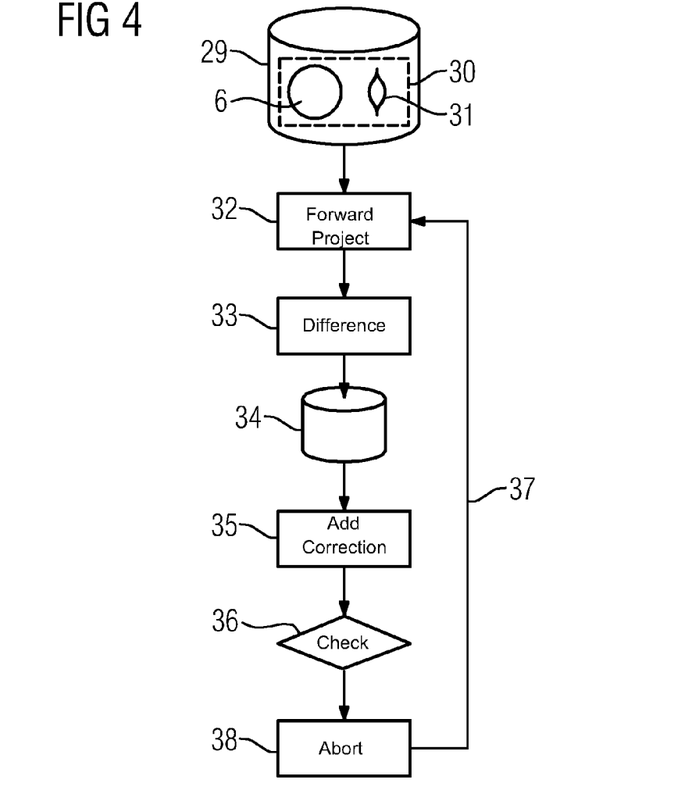
FIG. 4 is a flow diagram for the localization of the object in the second embodiment.

In the second embodiment, which is explained in more detail by FIG. 4, the localization of the areas 19 takes place within the context of an iterative, constantly improving reconstruction of the object 7 as well. To this end, an iterative procedure is used wherein a reconstruction data set is generated from the measured projection images 14, 18, although it relates to an enlarged object volume 30, which is indicated schematically in FIG. 4. The object volume 30 includes the reconstruction volume 6 and also an area that contains the object 7. As the area of the object 7 is not covered sufficiently in order to obtain a complete reconstruction since the object 7 may only be seen in some of the measured projection images 14, 18, the depiction 31 of the object 7 in the reconstruction data set 29 is imprecise, for example blurred, as indicated in FIG. 4.

It is now the object to improve the reconstruction data set 29 iteratively, for which, in an act 32, first comparative images are again forward-projected from the reconstruction data set 29, again for all projection directions of the measured projection images 14, 18 in question. However, in this case, these comparative images do not contain the object 7 concurrently with the areas 19, since, due to the insufficient cover, the depiction 31 is imprecise. Then, in an act 33, difference images describing the discrepancy between the depiction 31 and the actual object 7 are again formed for each projection direction in question by pixel-by-pixel subtraction. It is therefore possible to use the difference images to determine a correction data set 34 therefrom, which, in an act 35, is added to the reconstruction data set 29 in order to improve the reconstruction data set 29. In an act 36, it is checked whether an abort condition is exceeded. In the present case, two abort conditions are considered, namely, on the one hand, whether the L2 standard of the image data of the difference images, which is a measure of the discrepancy of the depiction 31 from the real object 7, is below a specific threshold value. In other words, it is optimized to obtain the smallest possible discrepancy from the actual object 7. A further, parallel abort condition considered provides a maximum number of possible iteration steps and is provided as a fallback solution. It also possible to use further abort conditions, for example an abort condition based on the L1 standard.

If no abort condition is fulfilled in act 36, the method is continued with act 32, arrow 37. However, if an abort condition is fulfilled, in act 38, the current, most recently determined reconstruction data set is used in order to segment the object 7 (or its now greatly improved depiction 31) therein by segmentation and then to determine the areas 19 by forward projection.

Figure 5:
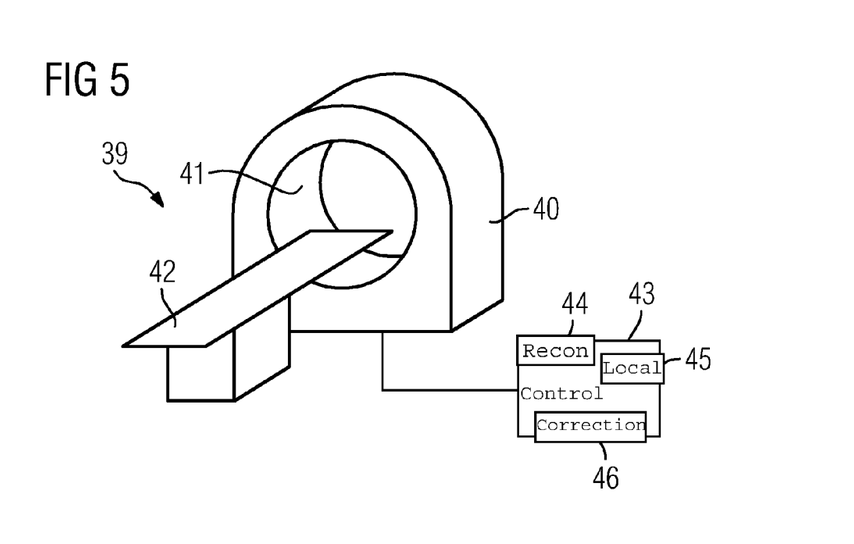
FIG. 5 is an X-ray device according to one embodiment.

FIG. 5 shows an X-ray device 39 according to one embodiment. The X-ray device 39 is here embodied as a CT device. The X-ray device 39 includes a gantry 40, in which the X-ray recording arrangement (not shown in any more detail here) with the X-ray tube and the X-ray detector may circle around a patient opening 41 into which a patient may be introduced by a patient couch 42.

The operation of the X-ray device 39 is controlled by a control device 43, which may also be integrated in the gantry 40 or elsewhere. The control device 43 is embodied to perform the method.

To this end, the control device 43 includes a reconstruction unit 44 for the reconstruction of the reconstruction data set 23, 29 from projection images, an object-localization unit 45 for the determination of the areas 19 according to the first or the second embodiment and a projection image correction unit 46 for correcting the projection images by removing the object and suitable interpolation.

Although the invention was illustrated and described in more detail by the preferred exemplary embodiments, the invention is not restricted by the disclosed examples and other variations may be derived herefrom by the person skilled in the art without departing from the scope of protection of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for reducing artifacts generated by at least one X-ray attenuating object arranged outside a reconstruction volume in a three-dimensional image data set showing the reconstruction volume, which is reconstructed from two-dimensional projection images recorded from different projection directions, the method comprising:
   localizing the object in the projection images showing the object; and
   determining corrected projection images for the reconstruction of the image data set, the image data of the area of each projection image showing the object being corrected to remove the object, wherein the localizing of the object is performed taking into account difference images of the measured projection images and from a reconstruction data set of forward-projected comparative images reconstructed from the measured projection images.

2. The method as claimed in claim 1, wherein localizing the object comprises localizing the object where the reconstruction volume is completely contained in all the projection images and the object has a higher density, higher attenuation coefficient, or the higher attenuation coefficient and the higher density than all naturally occurring materials in the body of a person.

3. The method as claimed in claim 2, wherein localizing the object comprises localizing a metal object.

4. The method as claimed in claim 1, wherein the reconstruction data set is determined by reconstruction of the reconstruction volume from the measured projection images.

5. The method as claimed in claim 4, wherein the area showing the object is segmented in the difference images.

6. The method as claimed in claim 5, wherein segmenting comprises using an edge detection algorithm.

7. The method as claimed in claim 5, further comprising segmenting the reconstruction data set according to at least two material classes with assigned attenuation coefficients, according to which a virtual normalization image based on effective transmission lengths of the material classes is determined in the projection directions of the projection images for which a comparative image is determined, and, prior to the formation of the difference images, the measured projection images and the comparative images are normalized using the normalization images, wherein the corrected measured projection images are denormalized after the removal of the object.

8. The method as claimed in claim 7, wherein the segmentation of the reconstruction data set is performed according to four material classes.

9. The method as claimed in claim 8, wherein the segmentation is performed according to air, soft tissue, bone, and contrast medium classes.

10. The method as claimed in claim 1, wherein the reconstruction data set is reconstructed for an object volume containing the object, the object volume being larger than the reconstruction volume, wherein, in an iterative method, in each case a three-dimensional correction data set is reconstructed from the difference images based on the current reconstruction data set and to form a new reconstruction data set added to the current reconstruction data set, wherein, following the introduction of an abort criterion, the object in the most recently determined reconstruction data set is segmented and the segmentation in the reconstruction data set is used for the localization of the object in the measured projection images.

11. The method as claimed in claim 10, wherein introducing the abort criterion comprises introducing a minimization of a statistical variable of the image data contained in the difference images, exceeding of a prespecified number of iterations, or both as an abort condition.

12. The method as claimed in claim 11, wherein introducing the minimization comprises introducing the minimization of an L1 standard or an L2 standard of the image data of the difference images as the statistical variable.

13. The method as claimed in claim 1, wherein artifacts generated by the object are detected in a reconstruction from the measured projection images based on the reconstruction volume and, from the geometric properties of the artifacts, a subset of the measured projection images is selected which subset may contain the areas showing the object, wherein the determination of the difference images a correction to remove the object is performed restricted to the subset.

14. The method as claimed in claim 13, wherein a Hough transformation is used for the detection of the artifacts.

15. The method as claimed in claim 13, wherein the artifacts detected are streak artifacts.

16. The method as claimed in claim 1, wherein for the determination of the corrected measured projection images, an interpolation is performed in the areas showing the object.

17. An X-ray device comprising:
an X-ray source;
an X-ray detector; and
a control device configured to:
   localize an object in a projection images showing the object;
   determine corrected projection images for the reconstruction of an image data set, the image data of an area of each projection image showing the object being corrected to remove the object, wherein the localizing of the object is performed taking into account difference images of the projection images and from a reconstruction data set of forward-projected comparative images reconstructed from the projection images.

18. The X-ray device of claim 17, wherein the control device is configured to:
segment the area showing the object in the difference images using an edge detection algorithm.

19. The X-ray device of claim 17, wherein the control device is configured to:
reconstruct the reconstruction data set for an object volume containing the object, the object volume being larger than the reconstruction volume, wherein, in an iterative method, in each case a three-dimensional correction data set is reconstructed from the difference images based on the current reconstruction data set and to form a new reconstruction data set added to the current reconstruction data set, wherein, following the introduction of an abort criterion, the object in the most recently determined reconstruction data set is segmented and the segmentation in the reconstruction data set is used for the localization of the object in the measured projection images.

20. A non-transitory computer readable storage medium having stored thereon instructions, the instructions when executed by a computing device:
localizing an object in projection images showing the object; and
determining corrected projection images for the reconstruction of an image data set, image data of the area of each projection image showing the object being corrected to remove the object, wherein the localizing of the object is performed taking into account difference images of the measured projection images and from a reconstruction data set of forward-projected comparative images reconstructed from the measured projection images.

* * * * *